US012693417B2

(12) United States Patent
Wang et al.

(10) Patent No.: US 12,693,417 B2
(45) Date of Patent: Jul. 28, 2026

(54) WATER QUALITY EARLY WARNING SYSTEM AND METHOD FOR AQUAPONICS BASED ON ZEBRAFISH BEHAVIOR ANALYSIS

(71) Applicant: China Agricultural University, Beijing (CN)

(72) Inventors: Cong Wang, Beijing (CN); Yang Hu, Beijing (CN); Daoliang Li, Beijing (CN); Yingyi Chen, Beijing (CN); Yaoguang Wei, Beijing (CN); Chunhong Liu, Beijing (CN)

(73) Assignee: China Agricultural University, Beijing (CN)

( * ) Notice: Subject to any disclaimer, the term of this patent is extended or adjusted under 35 U.S.C. 154(b) by 349 days.

(21) Appl. No.: 18/541,663

(22) Filed: Dec. 15, 2023

(65) Prior Publication Data

US 2024/0215545 A1 Jul. 4, 2024

(30) Foreign Application Priority Data

Dec. 28, 2022 (CN) ......................... 202211715064.0

(51) Int. Cl.
*G01S 17/50* (2006.01)
*G01N 33/18* (2006.01)

(52) U.S. Cl.
CPC .............. *G01S 17/50* (2013.01); *G01N 33/18* (2013.01)

(58) Field of Classification Search
CPC ........ G01S 17/50; G01N 33/18; A01G 31/02; Y02A 20/20; A01K 29/005; A01K 63/003; A01K 63/04
See application file for complete search history.

(56) References Cited

U.S. PATENT DOCUMENTS

2003/0163937 A1* 9/2003 Klotz ....................... G09F 19/08 40/426
2009/0163784 A1* 6/2009 Sarpeshkar ............. H03F 1/342 330/98
2017/0336381 A1* 11/2017 Zeevi ..................... G01N 29/02

FOREIGN PATENT DOCUMENTS

CN 213182818 U * 5/2021
CN 116171914 A * 5/2023 ............. A01K 61/95

OTHER PUBLICATIONS

Translation of CN 213182818 U (Year: 2021).*
Translation of CN 116171914 A (Year: 2022).*

* cited by examiner

*Primary Examiner* — Uzma Alam
*Assistant Examiner* — Mamadou Faye
(74) *Attorney, Agent, or Firm* — WCF IP

(57) ABSTRACT

A water quality early warning system and method for aquaponics based on zebrafish behavior analysis is provided. The system includes a monitoring chamber, an infrared transceiver array, a signal driving and collecting board and a processor, where the infrared transceiver array includes infrared transceiver modules; each infrared transceiver module includes an infrared transmitting module and an infrared receiving module; the signal driving and collecting board is connected to the infrared transceiver array, and configured to drive the infrared transmitting module to transmit infrared light, collect induced currents generated by the infrared receiving module and generate a voltage matrix in M rows and N columns according to induced currents; the processor is connected to the signal driving and collecting board, and configured to calculate motion parameters of the target zebrafish according to the voltage matrix, and perform an early warning on a water quality of the target water body.

11 Claims, 7 Drawing Sheets

WATER QUALITY EARLY WARNING SYSTEM AND METHOD FOR AQUAPONICS BASED ON ZEBRAFISH BEHAVIOR ANALYSIS

CROSS REFERENCE TO RELATED APPLICATION

This patent application claims the benefit and priority of Chinese Patent Application No. 202211715064.0 filed with the China National Intellectual Property Administration on Dec. 28, 2022, the disclosure of which is incorporated by reference herein in its entirety as part of the present application.

TECHNICAL FIELD

The present disclosure relates to the technical field of environmental engineering and aquaculture, and in particular to a water quality early warning system and method for aquaponics based on zebrafish behavior analysis.

BACKGROUND

Aquaponics system is an ecological circulation system that integrates fish culture and plant cultivation. In this system, fish and plants are interdependent, forming a mutually beneficial symbiotic relationship, that is, the fish provides nutrients from their waste to promote the growth of plants, while the plants absorb organic matters in the waste to maintain the water clean. When there is sudden pollution or drastic change in water quality, the aquaponics system collapses, causing serious economic losses. Therefore, it is a top priority to improve the aquaponics system and ensure economic benefits of the system by designing a water quality early warning method that can prevent water pollution accidents in the aquaponics system.

Currently, water quality monitoring and assessment methods are roughly divided into two categories. Category 1 is a physical and chemical analysis method that directly determines the content of a certain substance in a water sample using various instruments. This method requires a certain detection time, has a high detection cost, and has difficulty in achieving real-time continuous detection. Category 2 is a biological monitoring method that combines biological monitoring technology with environmental science. This method combines ecological and toxicological processes to evaluate water pollution using aquatic organisms' responses and feelings to a water environment, and shows an excellent real-time performance.

Zebrafish is a standard model organism for biological monitoring recommended by the International Standards Organization (ISO). The zebrafish has a wealth of toxicological data and is sensitive to a wide range of toxic substances. Moreover, this species has a lower cultivation cost, shows easier monitoring of behavioral patterns, and exhibits obvious stress responses. In the early 1990s, zebrafish began to be used for the detection of mixed compounds. Zebrafish can be used to conduct short- or long-term exposure experiments to a variety of environmental pollutants, even including carcinogens. It turns out that the zebrafish is more convenient as an experimental subject. However, in actual experiments, the behavior of zebrafish is not only interfered by water quality pollution factors, but also affected by water temperature, pH value, noise, light illumination and other factors, leading to abnormal behaviors. Even if the corresponding factors are controlled within a certain range, it is difficult to avoid irregular changes in the natural behaviors of the zebrafish caused by other uncontrollable factors.

At present, most of the main methods for water quality early warning using zebrafish biological monitoring are based on computer vision technology. Specifically, photos of the zebrafish behavior are recorded with a camera, and then through image analysis, the motion trajectory and other related motion data of the zebrafish are obtained for analysis. However, these methods are costly and require more resources for later image processing. In particular, there are currently a lot of repetitive and resource-wasting analysis methods, and there are also observation blind spots in the camera recording area.

SUMMARY

An objective of embodiments of the present disclosure is to provide a water quality early warning system and method for aquaponics based on zebrafish behavior analysis. The present disclosure aims to avoid observation blind spots in the existing water quality early warning technologies, reduce costs, and improve efficiency.

To achieve the above objective, the present disclosure provides the following technical solutions.

The present disclosure provides a water quality early warning system for aquaponics based on zebrafish behavior analysis, including:

- a monitoring chamber configured to house a target water body and a target zebrafish, where a detection module is provided in a center of the monitoring chamber, and the target water body and the target zebrafish are located outside the detection module;
- an infrared transceiver array, where the infrared transceiver array includes a plurality of infrared transceiver modules, and the plurality of infrared transceiver modules are arranged in M rows and N columns and are equally spaced on the detection module; each of the infrared transceiver modules includes an infrared transmitting module and an infrared receiving module; the infrared transmitting module is configured to transmit infrared light to the monitoring chamber, and the infrared receiving module is configured to generate an induced current based on the infrared light reflected by the monitoring chamber or the target zebrafish; where M is greater than or equal to 5, and N is greater than or equal to 12;
- a signal driving and collecting board connected to the infrared transceiver array, and configured to drive the infrared transmitting modules to transmit the infrared light, collect induced currents generated by the infrared receiving modules, and generate a voltage matrix in M rows and N columns according to the induced currents; and
- a processor connected to the signal driving and collecting board, and configured to continuously acquire the voltage matrix when the target zebrafish is in the target water body, calculate motion parameters of the target zebrafish according to the voltage matrix, and perform an early warning on a water quality of the target water body according to the motion parameters; where the motion parameters include: a motion speed, a motion acceleration, a depth of the zebrafish, a residence time, and a cumulative motion distance; and the cumulative motion distance is a total motion distance of the target zebrafish within a set recording time.

Optionally, the signal driving and collecting board includes:

an oscillation circuit configured to generate a square wave with a set frequency;

a power amplification circuit array connected to the oscillation circuit and the infrared transmitting modules, and configured to perform power amplification on the square wave and then drive the infrared transmitting modules to transmit the infrared light;

an I/V conversion circuit array connected to the infrared receiving modules, and configured to collect the induced currents generated by the infrared receiving modules, and then convert the induced currents into corresponding voltage signals; and a low-pass filter array connected to the I/V conversion circuit array and configured to filter the voltage signals to obtain the voltage matrix.

Optionally, the monitoring chamber is a cylindrical monitoring chamber made of a transparent material, and the detection module is a cylindrical detection module that is in a same height and coaxial with the monitoring chamber.

Optionally, M is 5 and N is 12; the infrared transceiver modules are equidistantly distributed at 5 different depths of the detection module, and 12 infrared transceiver modules are distributed at each depth at a same angle.

The present disclosure further provides a water quality early warning method for aquaponics based on zebrafish behavior analysis, where the water quality early warning method is applied to the above water quality early warning system, and includes the following steps:

continuously acquiring the voltage matrix when the target zebrafish is in the target water body, where the voltage matrix is generated by the signal driving and collecting board based on the induced currents generated by the infrared receiving modules in the infrared transceiver array;

calculating the motion parameters of the target zebrafish according to the voltage matrix, where the motion parameters include: the motion speed, the motion acceleration, the depth of the zebrafish, the residence time, and the cumulative motion distance; and the cumulative motion distance is the total motion distance of the target zebrafish within the set recording time; and performing the early warning on the water quality of the target water body according to the motion parameters.

Optionally, the calculating the motion parameters of the target zebrafish according to the voltage matrix includes:

calculating position information of the target zebrafish in the monitoring chamber according to the voltage matrix;

calculating a motion trajectory of the target zebrafish according to the position information; and calculating the motion parameters of the target zebrafish according to the motion trajectory.

Optionally, the calculating the position information of the target zebrafish in the monitoring chamber according to the voltage matrix includes:

comparing elements in the voltage matrix to obtain a maximum voltage, and determining a row number and a column number where the maximum voltage is located;

calculating a horizontal distance between the target zebrafish and the center of the monitoring chamber according to the maximum voltage; and calculating the position information of the target zebrafish in the monitoring chamber according to the row number, the column number, and the horizontal distance.

Optionally, the position information of the target zebrafish in the monitoring chamber is calculated according to the row number, the column number, and the horizontal distance by following formulas:

$$X = r\cos(j + 1)*360°/N;$$

$$Y = r\sin(j + 1)*360°/N; \text{ and}$$

$$Z = (i + 1)*h/M;$$

where i represents the row number, j represents the column number, r represents the horizontal distance between the target zebrafish and the center of the monitoring chamber, M represents a total number of rows of the elements in the voltage matrix, N represents a total number of columns of the elements in the voltage matrix, and h represents a depth of the monitoring chamber; and X represents a horizontal coordinate of the target zebrafish in the monitoring chamber, Y represents a longitudinal coordinate of the target zebrafish in the monitoring chamber, and Z represents a vertical coordinate of the target zebrafish in the monitoring chamber.

Optionally, the performing the early warning on the water quality of the target water body according to the motion parameters includes:

determining whether the motion speed is less than a set speed or whether the motion acceleration is less than a set acceleration to obtain a first determination result;

if the first determination result is NO, issuing an early warning of a sudden pollution of the water quality;

if the first determination result is YES, determining whether the depth of the zebrafish is greater than a first set depth to obtain a second determination result;

if the second determination result is NO, determining whether the residence time is less than a first set time to obtain a third determination result;

if the third determination result is NO, issuing an early warning of a serious pollution of the water quality;

if the third determination result is YES, determining whether the residence time is less than a second set time to obtain a fourth determination result, where the second set time is less than the first set time;

if the fourth determination result is NO, issuing an early warning of hypoxia of the water body;

if the fourth determination result is YES or the second determination result is YES, determining whether the depth of the zebrafish is less than a second set depth to obtain a fifth determination result, where the second set depth is greater than the first set depth;

if the fifth determination result is NO, determining whether the residence time is less than the second set time to obtain a sixth determination result;

if the sixth determination result is NO, issuing an early warning of an excessively low temperature of the water body;

if the sixth determination result is YES or the fifth determination result is YES, determining whether a recording time is greater than the set recording time to obtain a seventh determination result;

if the seventh determination result is NO, updating the recording time and returning to the step of "continuously acquiring the voltage matrix when the target zebrafish is in the target water body";

if the seventh determination result is YES, determining whether the cumulative motion distance is greater than a first set distance to obtain an eighth determination result;

if the eighth determination result is NO, issuing an early warning of a disease of the zebrafish;

if the eighth determination result is YES, determining whether the cumulative motion distance is less than a second set distance to obtain a ninth determination result, where the second set distance is greater than the first set distance;

if the ninth determination result is NO, issuing an early warning of a potential pollution of the water quality; and if the ninth determination result is YES, resetting the recording time and returning to the step of "continuously acquiring the voltage matrix when the target zebrafish is in the target water body".

Optionally, the set speed is 60 mm/s; the set acceleration is 130 mm/$s^2$; the first set depth is 0.1 times a depth of the monitoring chamber, and the second set depth is 0.9 times the depth of the monitoring chamber; the first set time is 30 min, and the second set time is 10 min; the set recording time is 24 h; and the first set distance is 40,000 cm, and the second set distance is 80,000 cm.

According to specific embodiments provided in the present disclosure, the present disclosure has the following technical effects.

The present disclosure provides a water quality early warning system and method for aquaponics based on zebrafish behavior analysis. In the present disclosure, a monitoring chamber is used to avoid observation blind spots in existing biological monitoring water quality early warning methods based on computer vision technology. Meanwhile, an infrared transceiver array including multiple infrared transmitting modules and multiple infrared receiving modules is used to locate a target zebrafish in the monitoring chamber. Moreover, a position of the target zebrafish is reflected in the form of a voltage matrix, and a motion parameter of the target zebrafish is calculated. In this way, an early warning of a water quality of a target water body is performed based on the motion parameter. The present disclosure has the advantages of low cost, high efficiency, simple structure, and convenient operation.

BRIEF DESCRIPTION OF THE DRAWINGS

To describe the technical solutions in embodiments of the present disclosure or in the prior art more clearly, the accompanying drawings required for the embodiments are briefly described below. Apparently, the accompanying drawings in the following description show merely some embodiments of the present disclosure, and those of ordinary skill in the art may still derive other accompanying drawings from these accompanying drawings without creative efforts.

Figure 1:
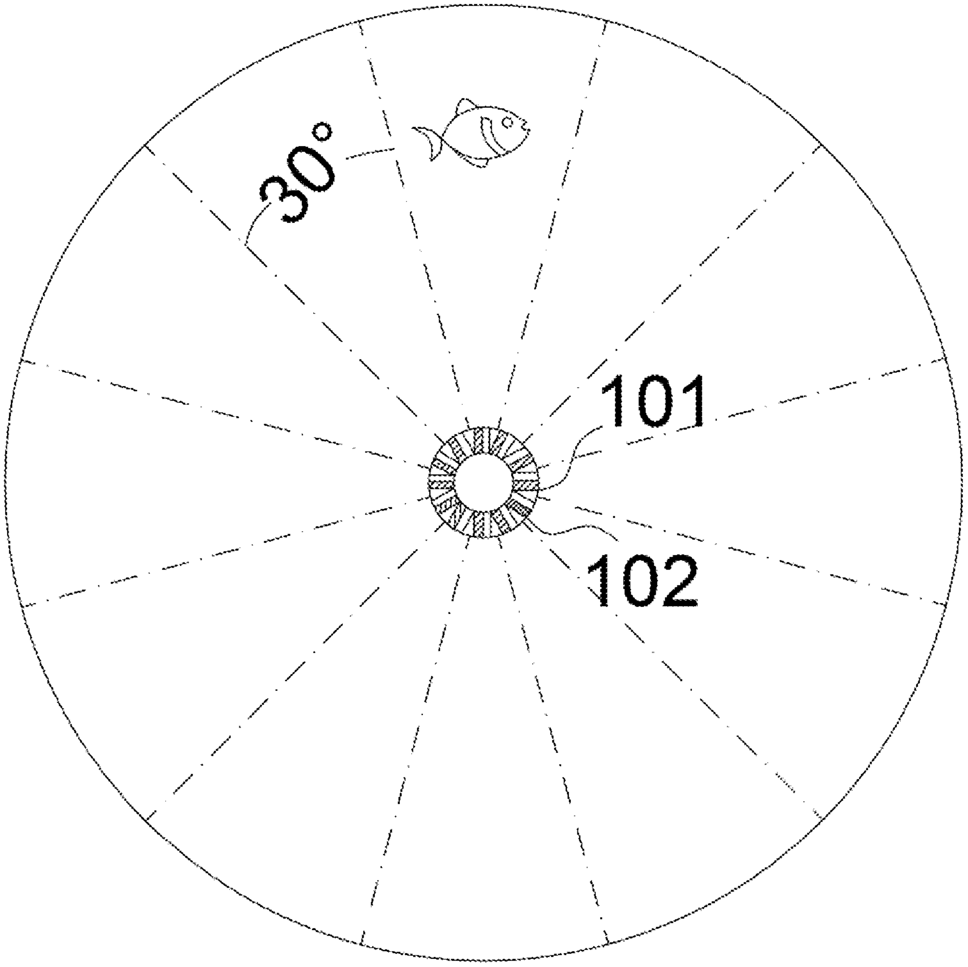
FIG. 1 shows a top view of a monitoring chamber according to an embodiment of the present disclosure.

Reference Numerals: infrared transmitting module—101, infrared receiving module—102, water hole—103, signal driving and collecting board—104, oscillation circuit—1041, power amplification circuit array—1042, I/V conversion circuit array—1043, low-pass filter array—1044, power management module—105, processor—106, and upper computer—107.

DETAILED DESCRIPTION OF THE EMBODIMENTS

The technical solutions of the embodiments of the present disclosure are clearly and completely described below with reference to the drawings in the embodiments of the present disclosure. Apparently, the described embodiments are merely a part rather than all of the embodiments of the present disclosure. All other embodiments obtained by those skilled in the art based on the embodiments of the present disclosure without creative efforts shall fall within the protection scope of the present disclosure.

An objective of embodiments of the present disclosure is to provide a water quality early warning system and method for aquaponics based on zebrafish behavior analysis. The present disclosure aims to avoid observation blind spots in the existing water quality early warning technologies, reduce costs, and improve efficiency.

In order to make the above objective, features and advantages of the present disclosure clearer and more comprehensible, the present disclosure will be further described in detail below in combination with accompanying drawings and particular implementations.

Figure 2:
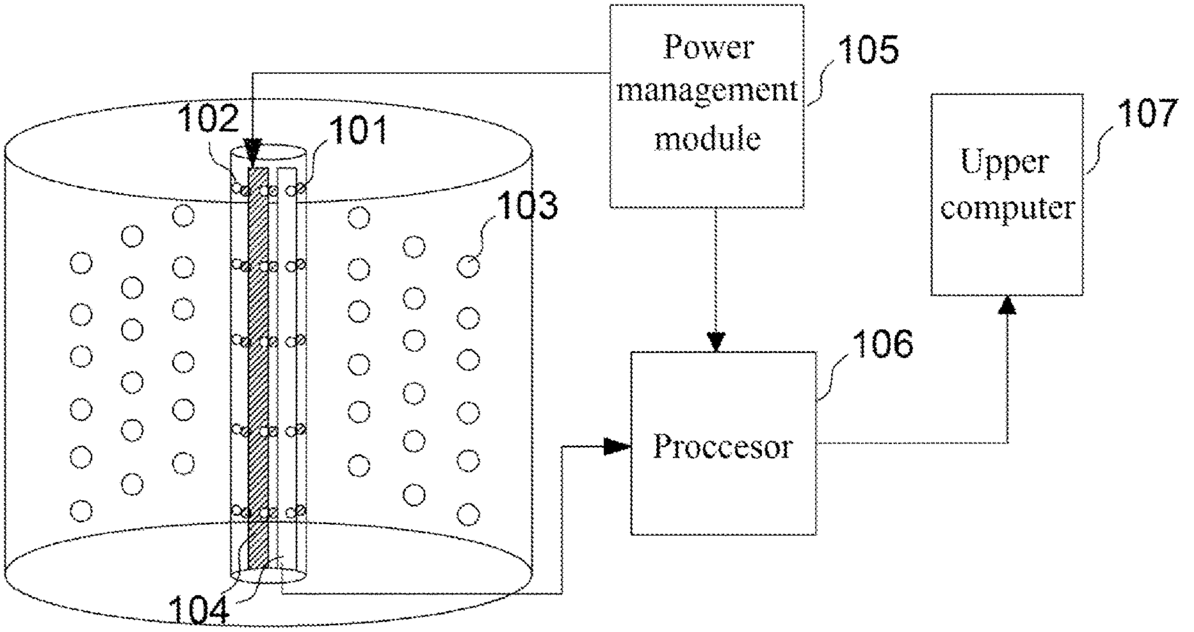
FIG. 2 shows a schematic structural diagram of a water quality early warning system according to an embodiment of the present disclosure.

As shown in FIG. 1 and FIG. 2, the present disclosure provides a water quality early warning system for aquaponics based on zebrafish behavior analysis. The water quality early warning system includes: a monitoring chamber, an infrared transceiver array, a signal driving and collecting board, and a processor.

The monitoring chamber is configured to house a target water body and a target zebrafish; where a detection module is provided in a center of the monitoring chamber, and the target water body and the target zebrafish are located outside the detection module.

The infrared transceiver array includes multiple infrared transceiver modules, and the multiple infrared transceiver modules are arranged in M rows and N columns and are equally spaced on the detection module. Each of the infrared transceiver modules includes an infrared transmitting module 101 and an infrared receiving module 102, and each infrared transmitting module 101 is configured to transmit infrared light to the monitoring chamber, and each infrared receiving module 102 is configured to generate an induced current based on the infrared light reflected by the monitoring chamber or the target zebrafish. Where M is greater than or equal to 5, and N is greater than or equal to 12. An interval angle between two adjacent infrared transceiver modules in a same row is 360°/N, and an interval distance between two adjacent infrared transceiver modules in a same column is h/(M+1), where h is a depth of the monitoring chamber.

The signal driving and collecting board 104 is connected to the infrared transceiver array, and configured to drive the infrared transmitting modules 101 to transmit the infrared light, collect the induced currents generated by the infrared receiving modules 102, and generate a voltage matrix in M rows and N columns according to the induced currents.

The processor 106 is connected to the signal driving and collecting board 104, and configured to continuously acquire the voltage matrix when the target zebrafish is in the target water body, calculate motion parameters of the target zebrafish according to the voltage matrix, and perform an early warning on a water quality of the target water body according to the motion parameters; where the motion parameters include: a motion speed, a motion acceleration, a depth of a zebrafish, a residence time, and a cumulative motion distance; and the cumulative motion distance is a total motion distance of the target zebrafish within a set recording time.

Optionally, the monitoring chamber is a cylindrical monitoring chamber made of a transparent material; and the detection module is a cylindrical detection module that is in a same height and coaxial with the monitoring chamber. Specifically, multiple water holes 103 are further arranged on an outer wall of the monitoring chamber; and the multiple water holes 103 are opened when a target water body needs to be replaced, and closed during the monitoring.

Figure 3:
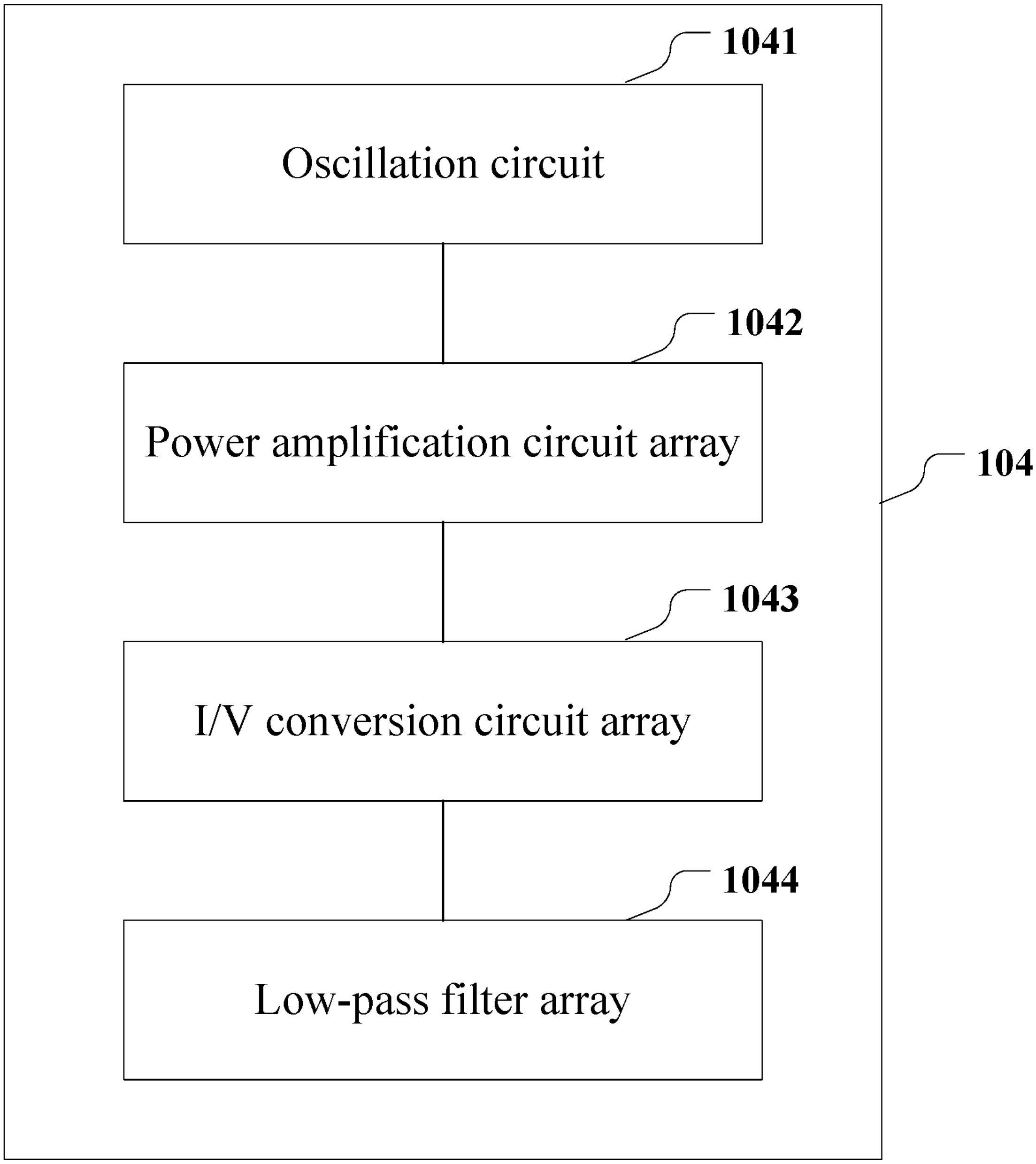
FIG. 3 shows a module structure diagram of a signal driving and collecting board according to an embodiment of the present disclosure.

Further, as shown in FIG. 3, the signal driving and collecting board 104 includes: an oscillation circuit 1041 configured to generate a square wave with a set frequency; a power amplification circuit array 1042 connected to the oscillation circuit 1041 and the infrared transmitting modules 101, and configured to perform power amplification on the square wave and then drive the infrared transmitting modules 101 to transmit the infrared light; an I/V conversion circuit array 1043 connected to the infrared receiving modules 102, and configured to collect the induced currents generated by the infrared receiving modules 102, and then convert the induced currents into corresponding voltage signals; and a low-pass filter array 1044 connected to the I/V conversion circuit array 1043 and configured to filter the voltage signals to obtain the voltage matrix. Optionally, the signal driving and collecting board 104 is located on the detection module.

As a specific implementation, the oscillation circuit 1041 is a 555 oscillation circuit; the infrared transmitting module 101 is an infrared transmitting LED or an infrared light-emitting diode; the infrared receiving module 102 is a photoelectric receiving tube; and the processor 106 is a microcontroller. The oscillation circuit 1041 generates a square wave of a certain frequency to control the power amplification circuit array 1042 to power the infrared transmitting LED or infrared light-emitting diode, which then transmits the infrared light. After the photoelectric receiving tube receives a reflected infrared light, a current signal collected is converted into a voltage signal through the I/V conversion circuit array 1043. The voltage signal is then filtered by the low-pass filter array 1044 and then input into the microcontroller for mathematical operations.

As a specific implementation, M is 5 and N is 12; that is, the infrared transceiver modules are equidistantly distributed at 5 different depths of the detection module, and 12 infrared transceiver modules are distributed at each depth at a same angle, with an interval angle of 360°/12=30°.

Further, the water quality early warning system further includes an upper computer 107. The upper computer 107 is connected to the processor 106 and is configured to display the motion parameters and perform data analysis and 3D model construction based on the motion parameters.

Specifically, a total of 60 infrared transmitting LEDs, together with an equal number of photoelectric receiving tubes 102, are placed at 5 different depths of the cylindrical detection module in the monitoring chamber, with a total of 12 modules at each depth, and there is an equal angle of 30° between each module, thereby dividing the monitoring chamber into 60 areas. Each group is connected to the signal driving and collecting board 104 on the detection module. The detection module collects an induced current Ir, which is converted into a voltage signal by the I/V conversion circuit array 1043, and then filtered by the low-pass filter array 1044 before being transmitted to the microcontroller. Position information of the target zebrafish is calculated and uploaded to the upper computer 107 to allow analysis and 3D model construction.

Further, the water quality early warning system further includes a power management module 105. The power management module 105 is connected to the signal driving and collecting board 104 and the processor 106; and the power management module 105 is configured to power the signal driving and collecting board 104 and the processor 106.

The present disclosure further provides a water quality early warning method for aquaponics based on zebrafish behavior analysis, where the water quality early warning method is applied to the water quality early warning system, and includes steps S1-S3.

In step S1, the voltage matrix when the target zebrafish is in the target water body is continuously acquired, where the voltage matrix is generated by the signal driving and collecting board based on the induced currents generated by the infrared receiving modules in the infrared transceiver array.

In step S2, the motion parameters of the target zebrafish are calculated according to the voltage matrix, where the motion parameters include the motion speed, the motion acceleration, the depth of the zebrafish, the residence time, and the cumulative motion distance; and the cumulative motion distance is the total motion distance of the target zebrafish within the set recording time.

In step S3, the early warning is performed on the water quality of the target water body according to the motion parameters.

Further, step S2 specifically includes steps S2.1-S2.3.

In step S2.1, position information of the target zebrafish in the monitoring chamber is calculated according to the voltage matrix, including: comparing elements in the voltage matrix to obtain a maximum voltage, and determining a row number and a column number where the maximum voltage is located; calculating a horizontal distance between the target zebrafish and the center of the monitoring chamber according to the maximum voltage; and calculating the position information of the target zebrafish in the monitoring chamber according to the row number, the column number, and the horizontal distance by the following formulas:

$$X = r\cos(j+1)*360°/N;$$

$$Y = r\sin(j+1)*360°/N; \text{ and}$$

$$Z = (i+1)*h/M;$$

where i represents the row number, j represents the column number, and r represents the horizontal distance between the target zebrafish and the center of the monitoring chamber; M represents a total number of rows of the elements in the voltage matrix, N represents a total number of columns of the elements in the voltage matrix, and h represents a depth of the monitoring chamber; and X represents a horizontal coordinate of the target zebrafish in the monitoring chamber, Y represents a longitudinal coordinate of the target zebrafish in the monitoring chamber, and Z represents a vertical coordinate of the target zebrafish in the monitoring chamber.

In step S2.2, a motion trajectory of the target zebrafish is calculated according to the position information.

In step S2.3, the motion parameter of the target zebrafish is calculated according to the motion trajectory.

Further, step S3 specifically includes following steps.

Whether the motion speed is less than a set speed or whether the motion acceleration is less than a set acceleration is determined to obtain a first determination result.

If the first determination result is NO, an early warning of a sudden pollution of the water quality is issued.

If the first determination result is YES, whether the depth of the zebrafish is greater than a first set depth is determined to obtain a second determination result.

If the second determination result is NO, whether the residence time is less than a first set time is determined to obtain a third determination result.

If the third determination result is NO, an early warning of a serious pollution of the water quality is issued.

If the third determination result is YES, whether the residence time is less than a second set time is determined to obtain a fourth determination result, where the second set time is less than the first set time.

If the fourth determination result is NO, an early warning of hypoxia of the water body is issued.

If the fourth determination result is YES or the second determination result is YES, whether the depth of the zebrafish is less than a second set depth is determined to obtain a fifth determination result, where the second set depth is greater than the first set depth.

If the fifth determination result is NO, whether the residence time is less than the second set time is determined to obtain a sixth determination result.

If the sixth determination result is NO, an early warning of an excessively low temperature of the water body is issued.

If the sixth determination result is YES or the fifth determination result is YES, whether a recording time is greater than the set recording time is determined to obtain a seventh determination result.

If the seventh determination result is NO, the recording time is updated, and it returns to the step of "continuously acquiring the voltage matrix when the target zebrafish is in the target water body".

If the seventh determination result is YES, whether the cumulative motion distance is greater than a first set distance is determined to obtain an eighth determination result.

If the eighth determination result is NO, an early warning of a disease of the zebrafish is issued.

If the eighth determination result is YES, whether the cumulative motion distance is less than a second set distance is determined to obtain a ninth determination result, where the second set distance is greater than the first set distance.

If the ninth determination result is NO, an early warning of a potential pollution of the water quality is issued.

If the ninth determination result is YES, the recording time is reset, and it returns to the step of "continuously acquiring the voltage matrix when the target zebrafish is in the target water body".

Optionally, the set speed is 60 mm/s; the set acceleration is 130 mm/$s^2$; the first set depth is 0.1 times a depth of the monitoring chamber, and the second set depth is 0.9 times the depth of the monitoring chamber; the first set time is 30 min, and the second set time is 10 min; the set recording time is 24 h; and the first set distance is 40,000 cm, and the second set distance is 80,000 cm.

Figure 4:
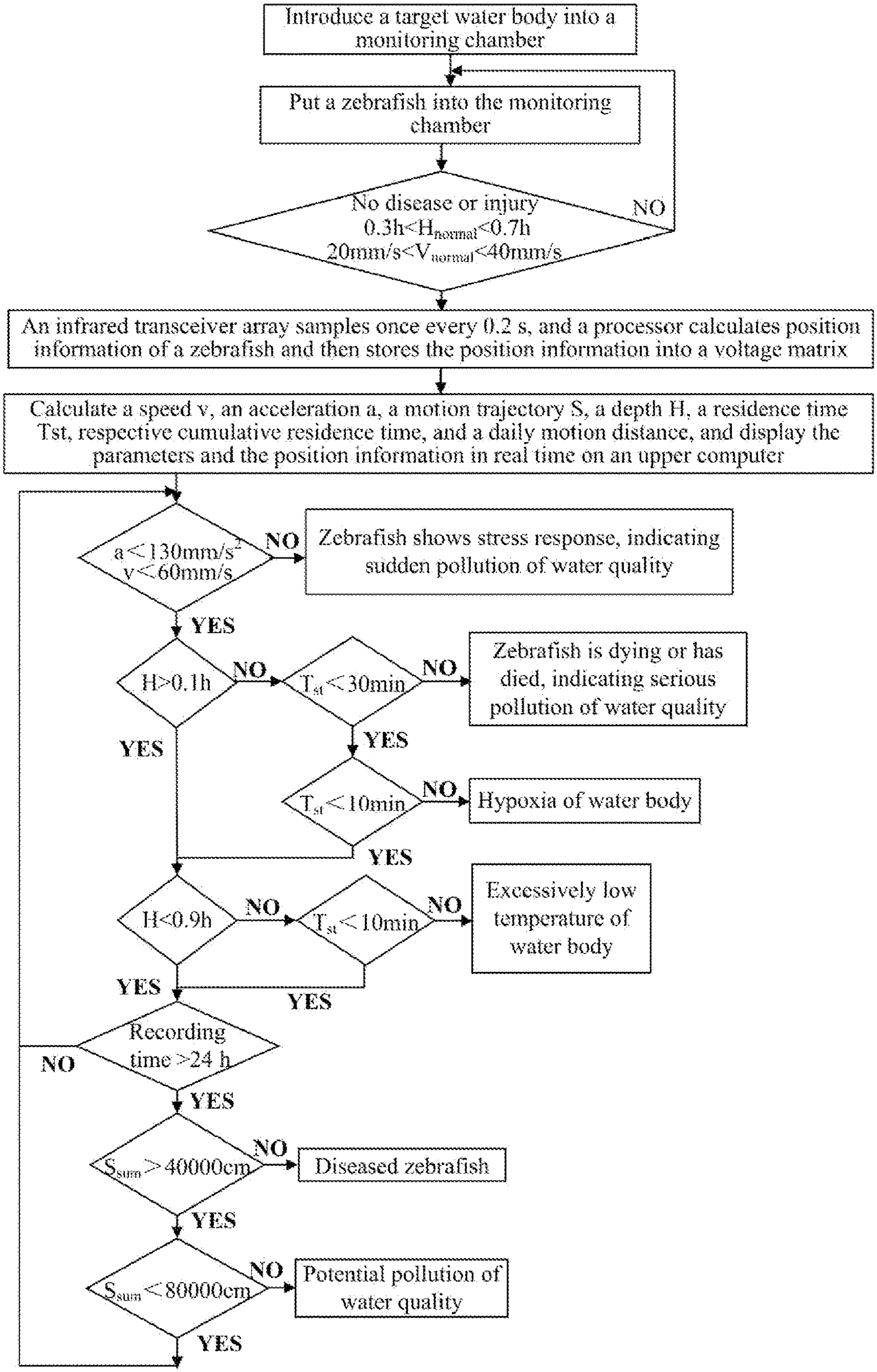
FIG. 4 shows a specific flow chart of a water quality early warning method according to an embodiment of the present disclosure.

In the present disclosure, a specific example of the water quality early warning method based on zebrafish behavior analysis was further provided, as shown in FIG. 4. The method included the following steps.

(1) A target water body was introduced into the monitoring chamber while maintaining circulation of the target water body; zebrafish individuals were selected with normal body color, no disease or injury, fast motion, and strong vitality; where under normal conditions for the individuals, a motion speed $v_{normal}$ should be at 20 mm/s to 40 mm/s, while a diving depth $H_{normal}$ should be at 0.3 h to 0.7 h (h was a depth of the monitoring chamber); if the selected individuals did not meet the conditions, appropriate individuals were reselected. If the zebrafish individuals adapted to the environment and showed no obvious stress response, it goes to a next step.

Figure 5:
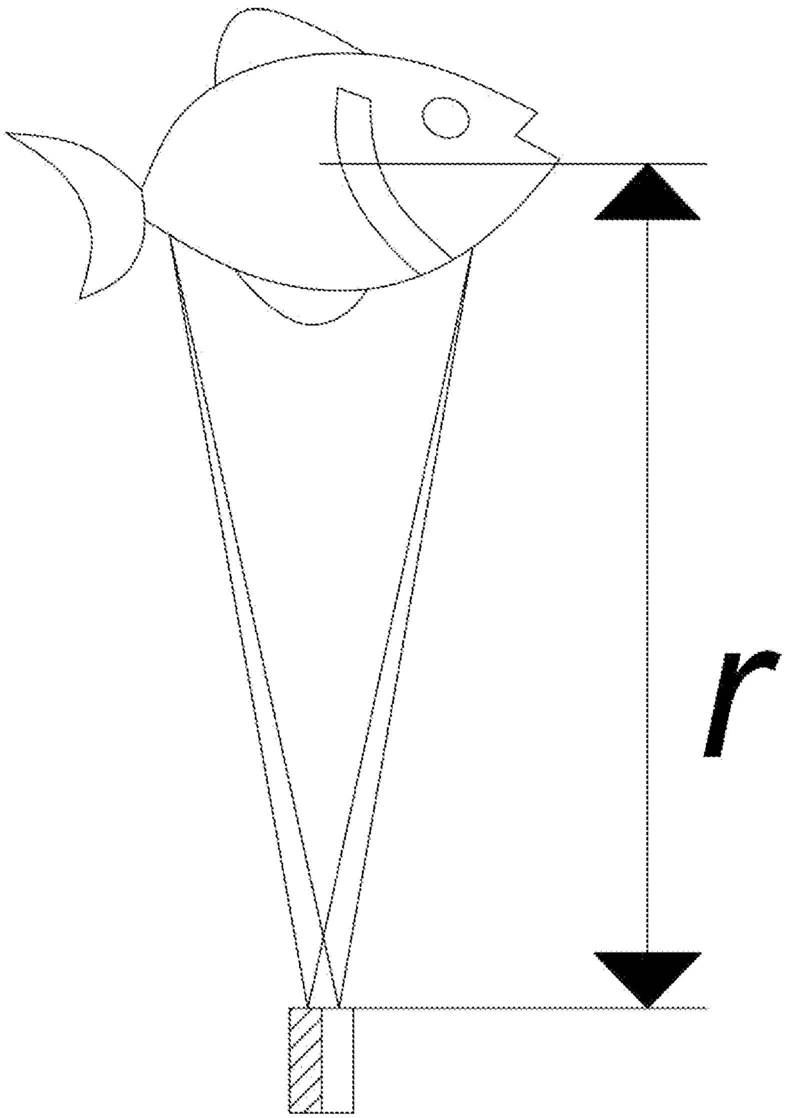
FIG. 5 is a schematic diagram showing a horizontal distance between a target zebrafish and a center of the monitoring chamber according to an embodiment of the present disclosure.

(2) The water quality early warning system was started to set a system sampling interval to 0.2 s; the infrared transmitting module started working, where 12 photoelectric receiving tubes at each group of depth corresponded to 12 groups of output voltages, and 5 depth samplings were completed to obtain 5×12 voltages; an ADC and a DMA in a microcontroller were used, and a conversion speed of the ADC was improved in combination with the method for sequentially switching analog switch chips (switching 5 times). The microcontroller processed data converted by the ADC and calculated a horizontal distance r from the zebrafish to the cylindrical detection module at a center of the monitoring chamber, as shown in FIG. 5.

Optionally, a calculation rule for the horizontal distance of the infrared transmitting module was as follows: after the infrared receiving module received a signal, it generated a corresponding induced current $I_r$, which was multiplied by K (an I/V conversion gain) to obtain a voltage $V_{out}$ before ADC conversion, and r was calculated based on $V_{out}=KI_r=ar^2+br+c$ (actual values of a, b, and c were measured through prior experiments). Alternatively, a voltage output by the signal driving and collecting board was directly used as $V_{out}$, and r was calculated based on a function relationship between $V_{out}$ and r measured experimentally.

Figure 6:
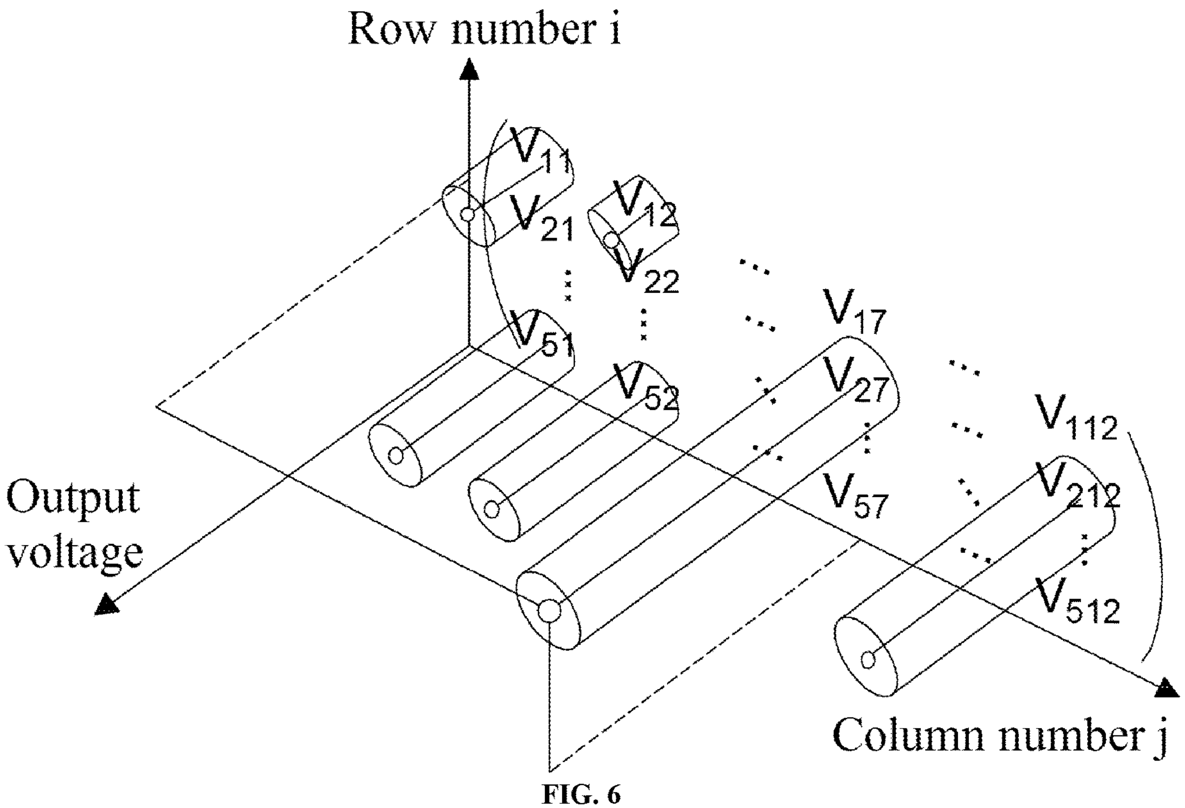
FIG. 6 is a schematic diagram showing a voltage matrix according to an embodiment of the present disclosure.
Figure 7:
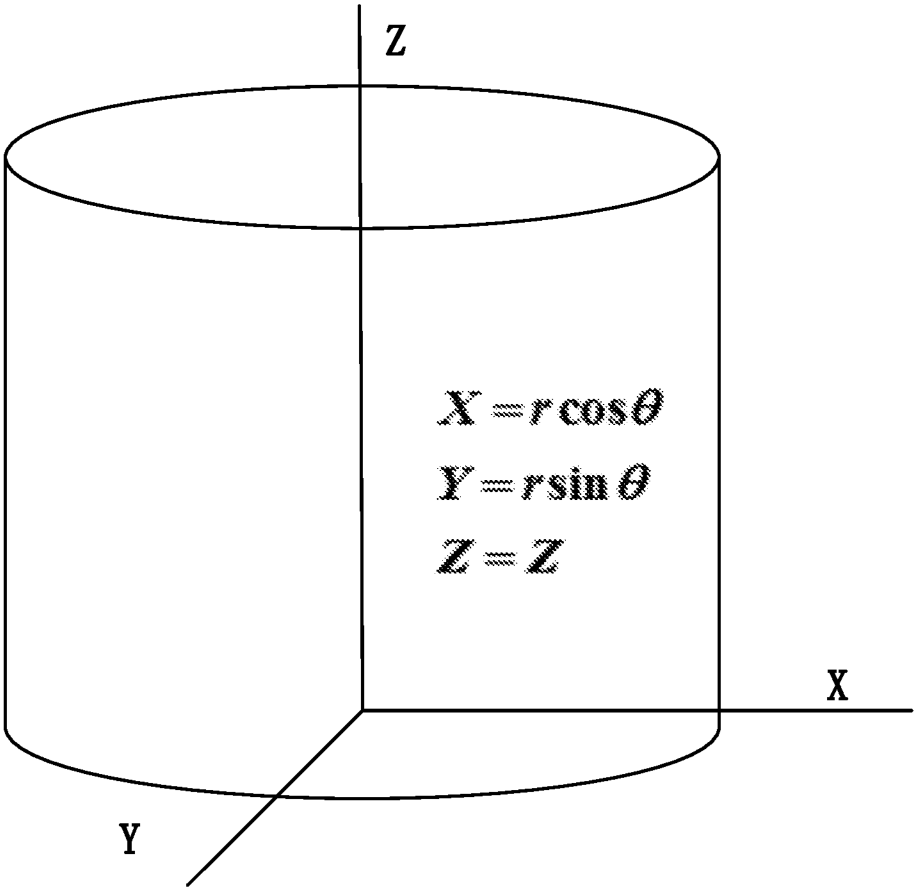
FIG. 7 is a schematic diagram showing coordinate transformation of position information of the target zebrafish in the monitoring chamber according to an embodiment of the present disclosure.

As shown in FIG. 6, a maximum value was found among 60 elements in the voltage matrix $$\begin{pmatrix} V_{11} & V_{12} & \dots & V_{17} & \dots & V_{112} \\ V_{21} & V_{22} & \dots & V_{27} & \dots & V_{212} \\ \vdots & \vdots & \ddots & \vdots & \dots & \vdots \\ V_{51} & V_{52} & \dots & V_{57} & \dots & V_{512} \end{pmatrix},$$

and a row number i and a column number j where the zebrafish was located were determined. As shown in FIG. 7, the coordinate system was converted: X=r cos θ, Y=r sin θ, r was a distance between the zebrafish and the center of the monitoring chamber, θ=(j+1)*30°, Z=(i+1)*h/5, to finally obtain the position information of the zebrafish (X, Y, Z).

(3) Based on the position information of two adjacent samplings, a rough motion trajectory S of the zebrafish during this period of time was obtained; S was divided by a sampling interval to obtain a motion speed v, and a difference between two adjacent motion speeds was divided by the sampling interval to obtain a motion acceleration a; a sampling interval in which the position did not change was recorded as a stagnation state to obtain a residence time $T_{st}$; a depth H of the zebrafish was directly recorded through the position information. Motion parameters were divided into real-time monitoring indicators and time-domain monitoring indicators. The real-time monitoring indicators included the motion speed v and motion acceleration a. When the motion speed v exceeded 60 mm/s or the motion acceleration exceeded 130 mm/s$^2$, it was considered that the zebrafish had a stress response and the water quality may have sudden pollution. The time-domain monitoring indicators included a daily motion distance $S_{sum}$, residence time $T_{st}$, and the depth H of the zebrafish. When H<0.1 h: if $T_{st}$ is >10 min, it was considered that the water body had hypoxia; if $T_{st}$ is >30 min, it meant that the zebrafish was dying or had died, indicating that the water quality had serious pollution. When H>0.9 h: if $T_{st}$ is >10 min, the water temperature was considered excessively low. All recorded motion trajectories were superimposed every day to obtain the daily motion distance $S_{sum}$. If the $S_{sum}$ was 40,000 cm to 80,000 cm, the water quality was considered normal. If the $S_{sum}$ was <40,000 cm, the target zebrafish was considered to be diseased. If the $S_{sum}$ was >80,000 cm, it was considered that there was potential pollution in the water quality.

(4) The microcontroller transmitted the position information of the zebrafish and the water quality to the upper computer. In software, a 3D model displayed the position of the zebrafish in the monitoring chamber in real time, the real-time monitoring indicators and the time-domain monitoring indicators were displayed in a status information bar, and information early warnings were given for possible water pollution or zebrafish diseases.

Each embodiment in the description is described in a progressive mode, each embodiment focuses on differences from other embodiments, and references can be made to each other for the same and similar parts between embodiments.

Particular examples are used herein for illustration of principles and implementations of the present disclosure. The descriptions of the above embodiments are merely used for assisting in understanding the method of the present disclosure and its core ideas. In addition, those of ordinary skill in the art can make various modifications in terms of particular implementations and the scope of application in accordance with the ideas of the present disclosure. In conclusion, the content of the description shall not be construed as limitations to the present disclosure.

What is claimed is:

1. A water quality early warning system for aquaponics based on zebrafish behavior analysis, comprising:

a monitoring chamber configured to house a target water body and a target zebrafish, wherein a detection module is provided in a center of the monitoring chamber, and the target water body and the target zebrafish are located outside the detection module;

an infrared transceiver array, wherein the infrared transceiver array comprises a plurality of infrared transceiver modules, and the plurality of infrared transceiver modules are arranged in M rows and N columns and are equally spaced on the detection module; the infrared transceiver modules comprise respective infrared transmitting modules and infrared receiving modules; each of the infrared transmitting modules is configured to transmit infrared light to the monitoring chamber, and each of the infrared receiving modules is configured to generate an induced current based on the infrared light reflected by the monitoring chamber or the target zebrafish;

a signal driving and collecting board connected to the infrared transceiver array, and configured to drive the infrared transmitting modules to transmit the infrared light, collect induced currents generated by the infrared receiving modules, and generate a voltage matrix in M rows and N columns according to the induced currents; and a processor connected to the signal driving and collecting board, and configured to continuously acquire the voltage matrix when the target zebrafish is in the target water body, calculate motion parameters of the target zebrafish according to the voltage matrix, and perform an early warning on a water quality of the target water body according to the motion parameters; wherein the motion parameters comprise: a motion speed, a motion acceleration, a depth of the zebrafish, a residence time, and a cumulative motion distance; and the cumulative motion distance is a total motion distance of the target zebrafish within a predetermined recording time, wherein M is 5 and Nis 12; the infrared transceiver modules are equidistantly distributed at 5 different depths of the detection module, and 12 infrared transceiver modules are distributed at each depth at a same angle.

2. The water quality early warning system according to claim 1, wherein the signal driving and collecting board comprises:

an oscillation circuit configured to generate a square wave with a predetermined frequency;

a power amplification circuit array connected to the oscillation circuit and the infrared transmitting modules, and configured to perform power amplification on the square wave and then drive the infrared transmitting modules to transmit the infrared light;

an I/V conversion circuit array connected to the infrared receiving modules, and configured to collect the induced currents generated by the infrared receiving modules, and then convert the induced currents into corresponding voltage signals; and a low-pass filter array connected to the I/V conversion circuit array and configured to filter the voltage signals to obtain the voltage matrix.

3. The water quality early warning system according to claim 1, wherein the monitoring chamber is a cylindrical monitoring chamber made of a transparent material, and the detection module is a cylindrical detection module that is in a same height and coaxial with the monitoring chamber.

4. A water quality early warning method for aquaponics based on zebrafish behavior analysis, wherein the water quality early warning method is applied to the water quality early warning system according to claim 1, and comprises:

continuously acquiring the voltage matrix when the target zebrafish is in the target water body, wherein the voltage matrix is generated by the signal driving and collecting board based on the induced currents generated by the infrared receiving modules in the infrared transceiver array;

calculating the motion parameters of the target zebrafish according to the voltage matrix, wherein the motion parameters comprise:

the motion speed, the motion acceleration, the depth of the zebrafish, the residence time, and the cumulative motion distance, wherein the cumulative motion distance is the total motion distance of the target zebrafish within the predetermined recording time; and performing the early warning on the water quality of the target water body according to the motion parameters.

5. The water quality early warning method according to claim 4, wherein the calculating the motion parameters of the target zebrafish according to the voltage matrix comprises:

calculating position information of the target zebrafish in the monitoring chamber according to the voltage matrix;

calculating a motion trajectory of the target zebrafish according to the position information; and calculating the motion parameters of the target zebrafish according to the motion trajectory.

6. The water quality early warning method according to claim 5, wherein the calculating the position information of the target zebrafish in the monitoring chamber according to the voltage matrix comprises:

comparing elements in the voltage matrix to obtain a maximum voltage, and determining a row number and a column number where the maximum voltage is located;

calculating a horizontal distance between the target zebrafish and the center of the monitoring chamber according to the maximum voltage; and calculating the position information of the target zebrafish in the monitoring chamber according to the row number, the column number, and the horizontal distance.

7. The water quality early warning method according to claim 6, wherein the position information of the target zebrafish in the monitoring chamber is calculated according to the row number, the column number, and the horizontal distance by following formulas:

$$X = r\cos(j + 1)*360°/N;$$

$$Y = r\sin(j + 1)*360°/N; \text{ and}$$

$$Z = (i + 1)*h/M;$$

wherein i represents the row number, j represents the column number, r represents the horizontal distance between the target zebrafish and the center of the monitoring chamber, M represents a total number of rows of the elements in the voltage matrix, N represents a total number of columns of the elements in the voltage matrix, h represents a depth of the monitoring chamber, X represents a horizontal coordinate of the target zebrafish in the monitoring chamber, Y represents a longitudinal coordinate of the target zebrafish in the monitoring chamber, and Z represents a vertical coordinate of the target zebrafish in the monitoring chamber.

8. The water quality early warning method according to claim 4, wherein the performing the early warning on the water quality of the target water body according to the motion parameters comprises:

determining whether the motion speed is less than a predetermined speed or whether the motion acceleration is less than a predetermined acceleration to obtain a first determination result;

if the first determination result is NO, issuing an early warning of a sudden pollution of the water quality;

if the first determination result is YES, determining whether the depth of the zebrafish is greater than a first predetermined depth to obtain a second determination result;

if the second determination result is NO, determining whether the residence time is less than a first predetermined time to obtain a third determination result;

if the third determination result is NO, issuing an early warning of a serious pollution of the water quality;

if the third determination result is YES, determining whether the residence time is less than a second predetermined time to obtain a fourth determination result, wherein the second predetermined time is less than the first predetermined time;

if the fourth determination result is NO, issuing an early warning of hypoxia of the water body;

if the fourth determination result is YES or the second determination result is YES, determining whether the depth of the zebrafish is less than a second predetermined depth to obtain a fifth determination result, wherein the second predetermined depth is greater than the first predetermined depth;

if the fifth determination result is NO, determining whether the residence time is less than the second predetermined time to obtain a sixth determination result;

if the sixth determination result is NO, issuing an early warning of an excessively low temperature of the water body;

if the sixth determination result is YES or the fifth determination result is YES, determining whether a recording time is greater than the predetermined recording time to obtain a seventh determination result;

if the seventh determination result is NO, updating the recording time and returning to the step of "continuously acquiring the voltage matrix when the target zebrafish is in the target water body";

if the seventh determination result is YES, determining whether the cumulative motion distance is greater than a first predetermined distance to obtain an eighth determination result;

if the eighth determination result is NO, issuing an early warning of a disease of the zebrafish;

if the eighth determination result is YES, determining whether the cumulative motion distance is less than a second predetermined distance to obtain a ninth determination result, wherein the second predetermined distance is greater than the first predetermined distance;

if the ninth determination result is NO, issuing an early warning of a potential pollution of the water quality; and if the ninth determination result is YES, resetting the recording time and returning to the step of "continuously acquiring the voltage matrix when the target zebrafish is in the target water body".

9. The water quality early warning method according to claim 8, wherein the predetermined speed is 60 mm/s;

the predetermined acceleration is 130 $mm/s^2$;

the first predetermined depth is 0.1 times a depth of the monitoring chamber, and the second predetermined depth is 0.9 times the depth of the monitoring chamber;

the first predetermined time is 30 min, and the second predetermined time is 10 min;

the predetermined recording time is 24 h; and the first predetermined distance is 40,000 cm, and the second predetermined distance is 80,000 cm.

10. The water quality early warning method according to claim 4, wherein the signal driving and collecting board comprises:

an oscillation circuit configured to generate a square wave with a predetermined frequency;

a power amplification circuit array connected to the oscillation circuit and the infrared transmitting modules, and configured to perform power amplification on the square wave and then drive the infrared transmitting modules to transmit the infrared light;

an I/V conversion circuit array connected to the infrared receiving modules, and configured to collect the induced currents generated by the infrared receiving modules, and then convert the induced currents into corresponding voltage signals; and a low-pass filter array connected to the I/V conversion circuit array and configured to filter the voltage signals to obtain the voltage matrix.

11. The water quality early warning method according to claim 4, wherein the monitoring chamber is a cylindrical monitoring chamber made of a transparent material, and the detection module is a cylindrical detection module that is in a same height and coaxial with the monitoring chamber.

* * * * *